United States Patent
Haar

(10) Patent No.: US 8,671,543 B2
(45) Date of Patent: Mar. 18, 2014

(54) MICRONEEDLE AND METHOD FOR THE PRODUCTION THEREOF

(75) Inventor: Hans-Peter Haar, Wiesloch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 47 days.

(21) Appl. No.: 13/311,705

(22) Filed: Dec. 6, 2011

(65) Prior Publication Data

US 2012/0310266 A1 Dec. 6, 2012

Related U.S. Application Data

(63) Continuation of application No. PCT/EP2010/058091, filed on Jun. 9, 2010.

(30) Foreign Application Priority Data

Jun. 10, 2009 (EP) ..................................... 09162464

(51) Int. Cl.
- *B21D 39/02* (2006.01)
- *B23P 11/00* (2006.01)
- *B21G 1/00* (2006.01)
- *A61B 5/00* (2006.01)
- *A61B 5/15* (2006.01)
- *A61B 5/151* (2006.01)

(52) U.S. Cl.
USPC .......... 29/428; 163/1; 163/4; 163/5; 600/583; 600/310; 600/365

(58) Field of Classification Search
USPC .................. 29/428; 163/1, 4, 5; 600/583, 310
See application file for complete search history.

(56) References Cited

U.S. PATENT DOCUMENTS

| 3,713,200 | A | | 3/1965 | Dunmire |
| 3,359,978 | A | * | 12/1967 | Smith, Jr. ...................... 604/161 |
| 4,377,165 | A | * | 3/1983 | Luther et al. .................. 604/160 |
| 4,672,734 | A | * | 6/1987 | Kawada et al. ................. 29/517 |

(Continued)

FOREIGN PATENT DOCUMENTS

| EP | 1 477 025 B1 | 8/1970 |
| EP | 1 323 483 A2 | 7/2003 |
| EP | 1 692 999 A1 | 8/2006 |
| WO | WO2008/122541 A1 | 10/2008 |

OTHER PUBLICATIONS

International Application No. PCT/EP2010/058091 International Preliminary Report on Patentability.

*Primary Examiner* — David Bryant
*Assistant Examiner* — Jun Yoo
(74) *Attorney, Agent, or Firm* — Woodard, Emhardt, Moriarty, McNett & Henry LLP

(57) ABSTRACT

In a process for producing a microneedle (12) that can be inserted into body tissue in which a needle tip (20) and a preferably capillary collecting channel (14) having a distal inlet for body fluid formed at the needle tip (20) are formed, it is provided that at least part of a preform (38) prefabricated from a flat material is shaped into a tubular structure (22) so that the collecting channel (14) is at least substantially annularly closed in the cross-section in the area of the tubular structure (22).

19 Claims, 2 Drawing Sheets

(56) References Cited

U.S. PATENT DOCUMENTS

| | | | |
|---|---|---|---|
| 4,785,868 A | 11/1988 | Koenig, Jr. | |
| 5,632,840 A * | 5/1997 | Campbell | 156/196 |
| 6,009,933 A * | 1/2000 | Doyle et al. | 163/5 |
| 6,915,821 B2 * | 7/2005 | Ooyauchi et al. | 138/177 |
| 8,052,618 B2 | 11/2011 | Haar et al. | |
| 2003/0009113 A1 | 1/2003 | Olson | |
| 2003/0028125 A1 * | 2/2003 | Yuzhakov et al. | 600/583 |
| 2009/0247841 A1 * | 10/2009 | Werner et al. | 600/310 |
| 2010/0010375 A1 * | 1/2010 | Haar et al. | 600/583 |
| 2010/0049091 A1 | 2/2010 | Haar | |

* cited by examiner

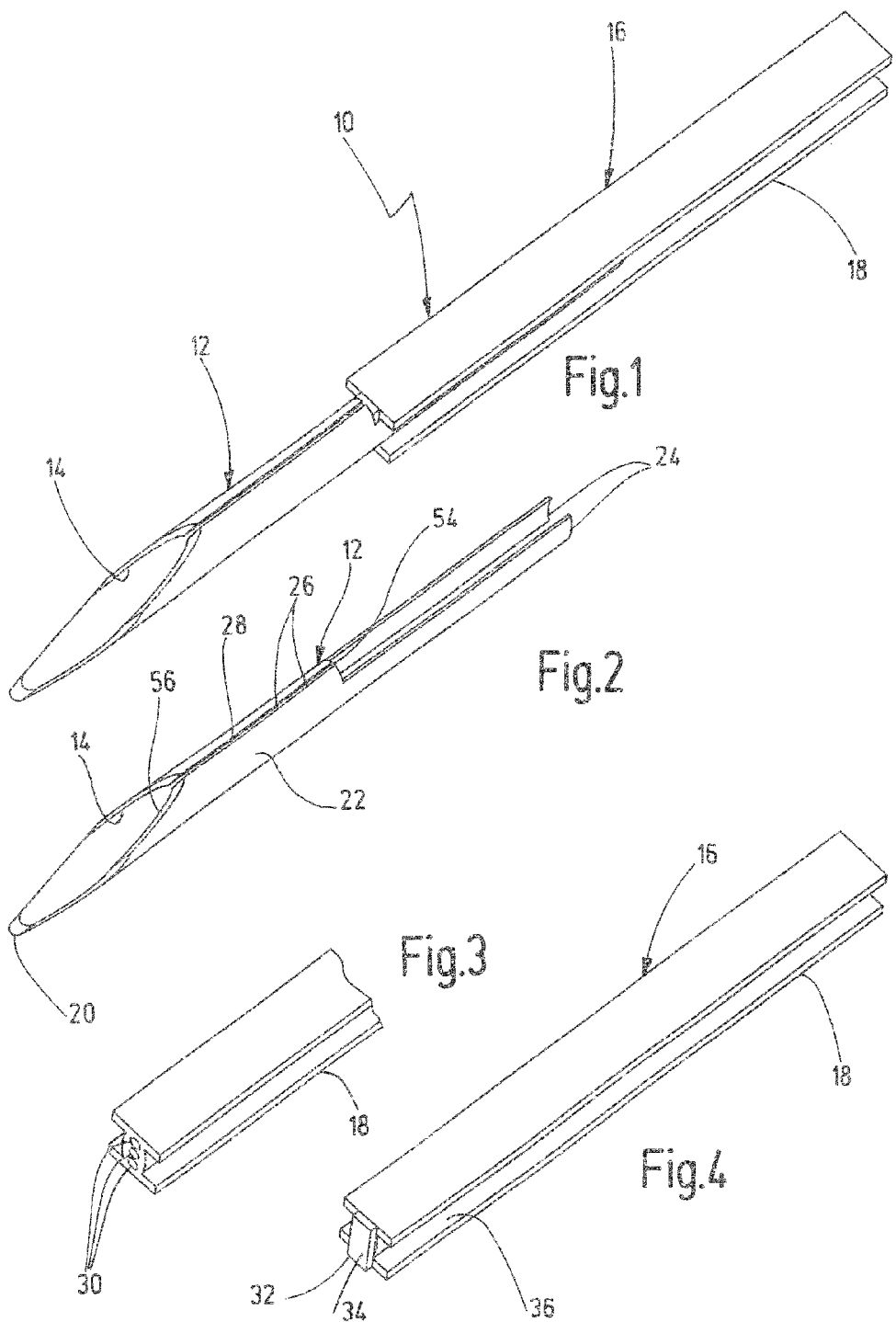

MICRONEEDLE AND METHOD FOR THE PRODUCTION THEREOF

CROSS REFERENCE TO RELATED APPLICATIONS

This application is a continuation of International Patent Application No. PCT/EP2010/058091, filed Jun. 9, 2010, which claims the benefit of European Patent Application No. 09162464.3 filed Jun. 10, 2009, which are hereby incorporated by reference.

DESCRIPTION

The invention concerns a process for producing a microneedle that can be inserted into body tissue in which a needle tip and a preferably capillary collecting channel having a distal inlet for body fluid formed at the needle tip are formed, wherein a preform made of a flat material is prefabricated. The invention additionally concerns a microneedle produced in this manner.

A generic process is known from WO 2008/122541. In this document it is proposed that a capillary-active collecting area for body fluid is defined by two bent parts that are folded towards one another. This means that after a skin puncture the user does not have to further check the sampling for a blood sugar measurement. At the same time a simplification of the manufacturing process is achieved in that the collecting area can be created without elaborate material processing steps such as those that would for example be required for removing material in the case of a wire material. However, the folding only creates a U-shaped channel structure that is only delimited on one half side where the evaporation of the liquid sample during capillary transport is still problematic particularly in the case of microscopic collection quantities. In this connection it should also be noted that the time window for collection and measurement has a lower limit in order to still ensure an adequate success of the measurement.

On this basis the object of the invention is to further improve the processes and devices known in the prior art and in particular to ensure a simple manufacturability with at the same time a high degree of safety of use especially for the mass production of analytical consumables.

The combination of features stated in the independent patent claims is proposed to achieve this object. Advantageous embodiments and further developments of the invention are derived from the dependent claims.

The invention is based on the idea of creating a 3D structure that is favourable for the intended use by shaping flat parts that are advantageous for the manufacturing process. Accordingly it is proposed according to the invention that at least a part of the preform is shaped into a tubular structure so that the collecting channel is at least substantially annularly or cylindrically closed in the cross-section in the area of the tubular structure. This creates a particularly favourable ratio of liquid volume to free surface so that the evaporation during sample processing can be considerably reduced. The tubular structure creates a circumferential boundary with the possible exception of a closing gap that is insignificant for evaporation, which is also advantageous for increasing the capillarity.

The tubular structure is preferably bent annularly while forming a longitudinal continuous closing gap thus creating a cylindrical collecting channel. For this it is advantageous when two outer edges of the preform which face away from one another are abutted and optionally the outer edges can be joined at least point-like by joining means and in particular by laser welding spots.

The production process is simplified by means of the fact that the preform is pressed by a form punch into a semi-open mould cavity of a forming tool where the mould cavity defines a partial contour of the tubular structure to be manufactured. Subsequently the tubular structure can be shaped by a closing punch pressed onto the free outer edges of the preform.

Alternatively it is also possible that the preform is pulled through a drawing die or a die plate where the drawing die has an opening defining the contour of the tubular structure.

It is also conceivable that the preform is formed from a plastic foil and is converted into the tubular structure by thermoforming.

For coupling to an automatic lancing and measuring device it is advantageous when a holding structure and in particular proximally projecting holding arms are moulded onto the preform.

Another advantageous embodiment provides that a plurality of preforms are prestructured as a contiguous composite preferably by etching or laser cutting.

In the sense of an increased system integration it is additionally advantageous when the collecting channel is connected at a proximal outlet distant from the needle tip to an analytical test element that reacts to a component of the body fluid to thus enable a one-step handling in particular for blood sugar determination. Advantageously a spreading element or a spreading membrane which distributes the collected body fluid two-dimensionally is attached to a proximal outlet of the collecting channel so that the available measuring area is enlarged. In this connection it is also advantageous when the preform is connected by means of a holding structure to an adapter carrying an analytical test element and/or light guide preferably by means of a plug connection.

For an improved adaptation to the test geometry it is advantageous when the tubular structure is provided with a proximal opening that deviates from a circular shape and in particular an elliptical proximal opening. In this connection it is also conceivable that the tubular structure is formed with a polygonal contour in particular by folding lines in the preform.

In order to enable a puncture that is as pain-free as possible, the needle tip can be formed on the preform by etching, cutting or grinding and/or can be made after formation of the tubular structure.

In order to further improve the liquid uptake, it is advantageous when a hydrophilic layer is applied at least to the inner side of the tubular structure.

The collecting channel is advantageously formed as a capillary flow path between the distal inlet and a proximal opening so that body fluid collected from the body tissue is transported by capillary action from the inlet away from the needle tip to the opening or the outlet. In this connection it is also advantageous when the collecting channel has a diameter in the range between 50 and 500 μm, preferably between 100 and 200 μm.

The invention also concerns a microneedle having an at least essentially circumferentially closed tubular structure which is formed from a flat preform.

BRIEF DESCRIPTION OF THE DRAWINGS

The invention is further elucidated in the following on the basis of embodiment examples shown schematically in the drawing.

FIG. 1 shows a microneedle with a sensor unit as a disposable microsampler for blood sugar determination in a perspective view.

FIG. 2 shows the microneedle according to FIG. 1.

FIG. 3 shows a section of the sensor unit according to FIG. 1 with integrated light guides.

FIG. 4 shows the sensor unit according to FIG. 1 with a frontal test element.

DETAILED DESCRIPTION

Figure 5:
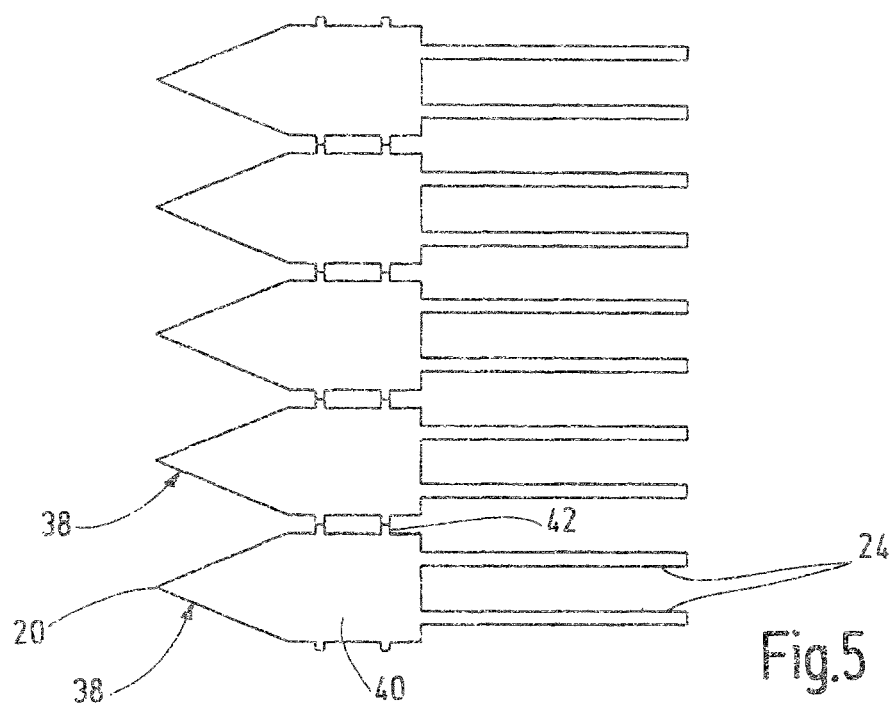
FIG. 5 shows a composite of flat shaped parts as preforms of microneedles in a top view.

The microsamplers 10 shown in FIG. 1 can be used as single-use articles for a blood sugar measurement in a hand-held device designed for them in order to collect a microscopic sample of blood and analyse it locally. For this purpose the microsamplers 10 comprise a microneedle 12 that can be inserted into the skin or body tissue, a collecting channel 14 formed thereon for taking up body fluid (blood and/or tissue fluid) obtained by the puncture through a distal inlet and a sensor unit 16 for a direct optical sample measurement. The sensor unit 16 has an adapter that can be coupled to a measuring device as described in WO 2008/122541 to which reference is herewith made in this connection.

As shown best in FIG. 2, the microneedle 12 has a tapered, flattened distal needle tip 20 as a lancing member, a capillary tubular structure 22 for the circumferential delimitation of the collecting channel 14 and two proximally projecting holding arms 24 for plugging it onto the adapter 18. The tubular structure 22 is annularly curved in cross-section and is cylindrically curved when viewed in the longitudinal direction, wherein the outer edges 26 are brought into abutment thereby forming the boundary of a continuous narrow closing gap 28. It is basically possible that the closing gap 28 is bridged by laser welding at least at certain points to further increase the structural stability.

FIG. 3 shows the distal end section of the adapter 18 with three parallel integrated light guides 30 for a reflectometric optical measurement. For this purpose a test element 32 is mounted on the distal ends of the light guides as shown in FIG. 4. In order to make a plug connection with the microneedle 12, its holding arms 24 can be inserted into lateral receiving grooves 36 of the adapter 18. Hence, the test element 32 is located at the proximal end of the flow path formed by the collecting channel 14. The cylindrical collecting channel 14 dispenses the liquid sample only at its end and should for this purpose have an inside diameter that is advantageously in the range between 100 and 200 µm. In the measuring state the detection layer 34 on the front side of the test element 32 is in fluidic contact with the proximal opening of the collecting channel 14 while a colour change that is based on a reaction with blood glucose can be detected optically from the rear side by means of the light guides 30. In order to ensure a terminal wetting, it is important that the blood fluid can be transported without evaporation losses which is essentially ensured by the laterally closed collecting channel 14.

Figure 6:
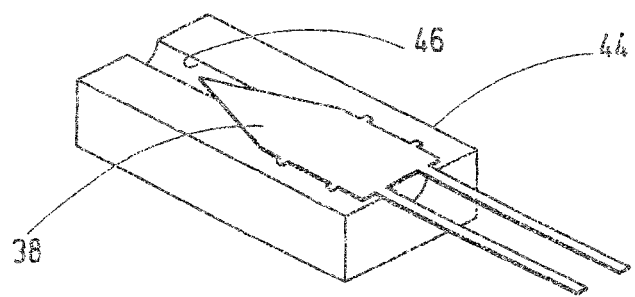
FIGS. 6 and 7 show a forming tool for shaping the preforms to form microneedles according to FIG. 2 in a diagrammatic representation.
Figure 7:
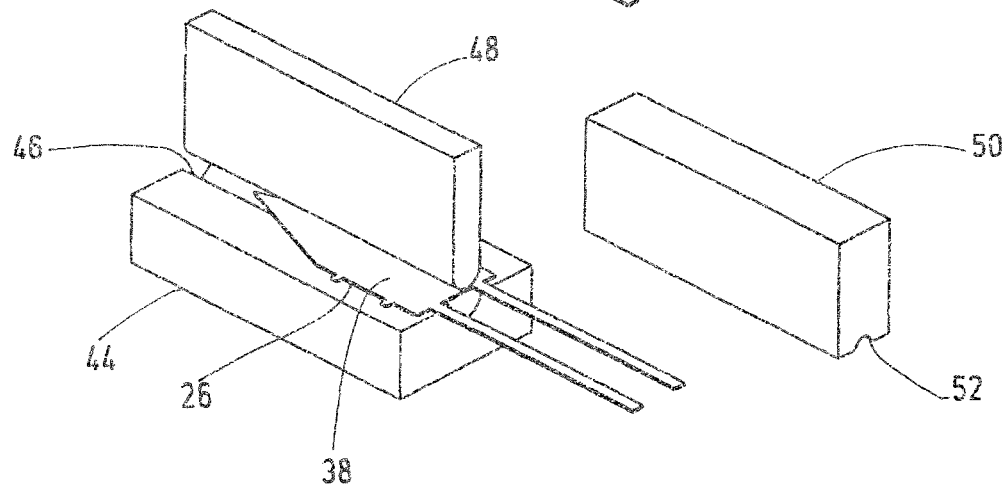

In order to enable a cost-effective mass production, the hollow structure is made from a flat material as illustrated in FIGS. 5 to 7.

FIG. 5 shows a composite of flat lancets as preforms 38 which can for example be formed from a stainless steel foil by an etching process or laser cutting so that the needle tip 20, the wall 40 of the tubular structure 22 and the holding arms 24 are already prestructured in the material plane. The preforms 38 can in this process still remain joined by material bridges 42.

In a subsequent shaping process the preforms 38 are positioned individually on a forming tool 44 as shown in FIG. 6. The forming tool 44 has a semi-open approximately U-shaped mould cavity 46 which defines a partial contour of the tubular structure to be manufactured.

The bending deformation then takes place by means of the punches 48, 50 according to FIG. 7. Firstly the preform 38 is pressed downwards by the preform punch 48 into the mould cavity 46 to emboss the lower half side of the tubular structure 22. Then the closing punch 50 is pressed onto the upwards projecting outer edges 26 in order to annularly close the upper half side of the tubular structure 22 corresponding to the frontal contour 52 of the closing punch 50. The moulded part produced in this manner then corresponds to the microneedle according to FIG. 2. The needle tip 20 can optionally be additionally sharpened by post-machining and in particular by grinding.

The tubular structure 22 can have a continuous circular cross-section. In order to adapt it to the rectangular shape of the test element 32 it is also possible to flatten the proximal area so that an oval or elliptical outlet opening 54 is achieved. The wall constriction also increases the capillarity in the transport direction which facilitates a reliable wetting of the test element 32. In this connection it is also advantageous when the inner side of the tubular structure 22 is provided with a hydrophilic layer 56 which can already be applied in the course of the machining of the flat material as a flow path for the body fluid.

The invention claimed is:

1. Process for producing a microneedle that can be inserted into body tissue in which a needle tip and a capillary collecting channel having a distal inlet for body fluid formed at the needle tip are formed, the process comprising:
   a) a preform is prefabricated of a flat material,
   b) proximally projecting holding arms are formed on the preform as a holding structure,
   c) at least a part of the preform is shaped into a tubular structure so that the collecting channel is at least substantially annularly closed in the cross-section in the area of the tubular structure, and
   d) the preform is connected by means of the holding structure to an adapter carrying an analytical test element and/or light guides.

2. Process according to claim 1, characterized in that a cross-section of the tubular structure is bent annularly while forming a longitudinal continuous closing gap.

3. Process according to claim 1, characterized in that two outer edges of the preform which face away from one another are abutted and the outer edges are joined at least point-like by joining means or by laser welding spots.

4. Process according to claim 1, characterized in that the preform is pressed by a form punch into a semi-open mould cavity of a forming tool where the mould cavity defines a partial contour of the tubular structure to be manufactured.

5. Process according to claim 1, characterized in that the tubular structure is shaped by a closing punch pressed onto the free outer edges of the preform.

6. Process according to claim 1, characterized in that the preform is pulled through a drawing die, where the drawing die has an opening defining the contour of the tubular structure.

7. Process according to claim 1, characterized in that the preform is formed from a plastic foil and is converted into the tubular structure by thermoforming.

8. Process according to claim 1, characterized in that a plurality of preforms are prestructured as a contiguous composite preferably by etching or laser cutting.

9. Process according to claim 1, characterized in that the collecting channel is connected at a proximal outlet to an analytical test element that reacts to a component of the body fluid.

10. Process according to claim 1, characterized in that a spreading element which distributes the collected body fluid two-dimensionally is attached to a proximal outlet of the collecting channel.

11. Process according to claim 1, characterized in that the preform is connected by means of the holding structure to the adapter carrying the analytical test element and/or light guides by means of a plug connection.

12. Process according to claim 1, characterized in that the tubular structure is provided with an in particular elliptical proximal opening that deviates from a circular shape.

13. Process according to claim 1, characterized in that the tubular structure is formed with a polygonal contour in particular by folding lines in the preform.

14. Process according to claim 1, characterized in that the needle tip is formed on the preform by etching, cutting or grinding and/or made after formation of the tubular structure.

15. Process according to claim 1, characterized in that a hydrophilic layer is applied at least to the inner side of the tubular structure.

16. Process according to claim 1, characterized in that collecting channel is formed as a capillary flow path between the distal inlet and a proximal outlet so that body fluid is transported by capillary action from the inlet to the outlet.

17. Process according to claim 1, characterized in that the collecting channel is formed with a diameter in the range between 50 and 500 µm, preferably between 100 and 200 µm.

18. A process for producing a microneedle that can be inserted into body tissue in which a needle tip and a capillary collecting channel having a distal inlet for body fluid formed at the needle tip are formed, the process comprising:
 a) a preform is prefabricated of a flat material,
 b) a pair of proximally projecting holding arms are formed on the preform as a holding structure,
 c) at least a part of the preform is shaped into a tubular structure so that the collecting channel is at least substantially annularly closed in the cross-section in the area of the tubular structure, and
 d) the preform is connected by means of the holding structure inserted into a pair of lateral receiving grooves on an adapter carrying an analytical test element and/or light guides.

19. A process for producing a microneedle that can be inserted into body tissue in which a needle tip and a capillary collecting channel having a distal inlet for body fluid formed at the needle tip are formed, the process comprising:
 a) a preform is prefabricated of a flat material,
 b) a first proximally projecting holding arm and a second proximally projecting holding arm are formed on the preform as a holding structure, wherein the first proximally projecting holding arm is substantially parallel to the second proximally projecting holding arm,
 c) at least a part of the preform is shaped into a tubular structure so that the collecting channel is at least substantially annularly closed in the cross-section in the area of the tubular structure, and
 d) the preform is connected by means of the holding structure to an adapter carrying an analytical test element and/or light guides.

* * * * *